United States Patent
Hess (10) Patent No.: US 12,178,932 B2
(45) Date of Patent: Dec. 31, 2024

(54) DISINFECTION APPARATUS FOR TRANSPORT CONTAINERS OF AN INSPECTION ARRANGEMENT

(71) Applicant: SMITHS DETECTION GERMANY GMBH, Wiesbaden (DE)

(72) Inventor: Gregor Hess, Wiesbaden (DE)

(73) Assignee: SMITHS DETECTION GERMANY GMBH, Wiesbaden (DE)

( * ) Notice: Subject to any disclaimer, the term of this patent is extended or adjusted under 35 U.S.C. 154(b) by 215 days.

(21) Appl. No.: 17/923,457

(22) PCT Filed: May 5, 2021

(86) PCT No.: PCT/EP2021/061870
§ 371 (c)(1),
(2) Date: Nov. 7, 2022

(87) PCT Pub. No.: WO2021/224330
PCT Pub. Date: Nov. 11, 2021

(65) Prior Publication Data
US 2023/0190975 A1 Jun. 22, 2023
US 2024/0066167 A9 Feb. 29, 2024

(30) Foreign Application Priority Data
May 7, 2020 (DE) .......................... 102020112465.1

(51) Int. Cl.
*A61L 2/24* (2006.01)
*A61L 2/10* (2006.01)
(Continued)

(52) U.S. Cl.
CPC ...... *A61L 2/24* (2013.01); *A61L 2/10* (2013.01); *A61L 2/22* (2013.01); *G01N 23/04* (2013.01);
(Continued)

(58) Field of Classification Search
CPC ..... A61L 2/24; A61L 2/10; A61L 2/22; A61L 2202/11; A61L 2202/15; A61L 2202/17;
(Continued)

(56) References Cited

U.S. PATENT DOCUMENTS

| 2008/0289649 A1 | 11/2008 | Woytkiw |
| 2015/0190538 A1 | 7/2015 | Olvera et al. |
| 2016/0376046 A1* | 12/2016 | Clusserath .............. A61L 2/025 422/20 |

FOREIGN PATENT DOCUMENTS

| DE | 102011103767 A1 | 9/2012 |
| DE | 102012103116 A1 | 10/2013 |

(Continued)

OTHER PUBLICATIONS

PCT International Search Report and Written Opinion, Application No. PCT/EP2021/061870, dated Aug. 27, 2021, 12 pages: with English translation.

(Continued)

*Primary Examiner* — Kiho Kim
(74) *Attorney, Agent, or Firm* — Armstrong Teasdale LLP (57) ABSTRACT

Proposed is a disinfection device for automatically disinfecting a transport container intended for transporting one or more inspection objects through an inspection apparatus and non-destructively inspecting them in the inspection apparatus, the disinfection device including: an input point connected to a pick-up point, an output point connected to a lay-up point, and at least one return device extending from the input point to the output point, and at least one automatic disinfection device arranged at the return path for disinfecting the emptied transport containers.

20 Claims, 4 Drawing Sheets

(51) Int. Cl.
  *A61L 2/22*      (2006.01)
  *G01N 23/04*     (2018.01)
  *G01N 23/083*    (2018.01)
  *G01N 23/10*     (2018.01)

(52) U.S. Cl.
  CPC ........... *G01N 23/083* (2013.01); *G01N 23/10* (2013.01); *A61L 2202/11* (2013.01); *A61L 2202/15* (2013.01); *A61L 2202/17* (2013.01); *A61L 2202/23* (2013.01); *G01N 2223/643* (2013.01)

(58) Field of Classification Search
  CPC ....... A61L 2202/23; A61L 2/18; G01N 23/04; G01N 23/083; G01N 23/10; G01N 2223/643; B65G 47/248
  See application file for complete search history.

(56) References Cited

FOREIGN PATENT DOCUMENTS

EP      1588720 A1    10/2005
KR    20200017996 A    2/2020

OTHER PUBLICATIONS

German Search Report, Application No. 102020112465.1, dated Apr. 30, 2021, 8 pps.

* cited by examiner

DISINFECTION APPARATUS FOR TRANSPORT CONTAINERS OF AN INSPECTION ARRANGEMENT

CROSS-REFERENCE TO RELATED APPLICATIONS

This application is a national stage application of PCT/EP2021/061870 filed on May 5, 2021, which claims priority to DE Application No. 102020112465.1 filed on May 7, 2020, the disclosures of which are hereby incorporated by reference herein in their entirety as part of the present application.

TECHNICAL FIELD

The present disclosure relates generally to an arrangement for disinfecting containers. More particularly, the present disclosure relates to an arrangement for automatically disinfecting transport containers used at an inspection apparatus for holding inspection objects. Further, the present disclosure relates to an inspection arrangement for inspecting objects, such as carry-on luggage and other objects carried by persons, in combination with the arrangement for automatically disinfecting the transport containers.

BACKGROUND OF THE PRESENT DISCLOSURE

For the security control of hand luggage and other objects carried by persons, for example during the security control at checkpoints at airports, inspection apparatuses for non-destructive inspection, for example X-ray inspection apparatuses, are known to be used, in which the objects carried as inspection objects are radiographed with X-ray beams. The primary goal of the inspection is to find dangerous objects, such as weapons or explosives, but also illegal objects, such as drugs or contraband.

The inspection objects are conveyed through the inspection apparatus, which is operated by an operator, on a conveyor, usually a conveyor belt. Typically, a lay-up point for the inspection objects is located on an input side in front of the conveyor, which is usually designed as a belt conveyor. Accordingly, on the output side behind the inspection apparatus there is a pick-up point from which the inspected inspection objects can be picked up. For example, a slightly sloping roller conveyor can lead from the transport device to the pick-up point, on which the inspected inspection objects move automatically to the pick-up point or can simply be moved manually.

For the transport of small inspection objects (such as wallets, cell phones, laptops, small backpacks, etc.) and pieces of clothing, transport containers, for example in the form of transport bins, are known to be used in which inspection objects are placed. Like larger inspection objects (for example bags, trolleys, carry-on suitcases, etc.), the transport containers with the inspection objects inside are positioned at a lay-up point, transferred to the transport apparatus, and conveyed by it through the inspection apparatus. After the non-destructive inspection, the inspected and unsuspicious inspection objects are picked up again from the transport container at the pick-up point by their owner, for example a passenger. After emptying, the transport containers are returned to the input of the inspection arrangement. For this purpose, they are either carried back by the operating personnel or returned to the lay-up point by a motorized return system.

During operation, at an airport checkpoint, the transport containers are filled and emptied with different items by different people. In addition to electronic devices and small bags, passengers are encouraged to place liquids, chemical substances such as cosmetics or medications, and even their own worn and thus dirty shoes (e.g., boots) into the transport containers for their inspection.

Due to the high number of people using or touching the transport containers, the surfaces of the transport containers are exposed to a high level of contamination with impurities, but also microorganisms. A specialist study has shown that the surfaces of transport containers at airports, for example, have influenza viruses A and B, coronaviruses, and adenoviruses and rhinoviruses, and can thus be a vector for the transmission of the associated diseases. This would make checkpoints at airports not only transportation hubs, but potentially hotspots for the spread of pathogens.

The current standard measure to mitigate this risk is to periodically remove transport containers from use at the checkpoint and manually clean and disinfect them elsewhere. This is not a perfect solution. Since each checkpoint has a limited number of transport containers, it would not be practical to disinfect each transport bin after each use without too much impact on the smooth flow and throughput at a checkpoint.

DE 10 2006 006 208 B4 and DE 10 2010 026 940 A1 of the same applicant show examples of inspection arrangements known per se with at least one inspection apparatus as well as transport apparatuses for the above-mentioned transport containers for holding inspection objects.

BRIEF DESCRIPTION

The present disclosure provides systems and methods by which the surficial load of transport containers can be kept at the same low level as far as possible over the course of time without impairing the operation at an inspection arrangement (checkpoint) and thus to prevent or at least reduce the risk of spreading pathogens and germs.

A key idea of the solution proposed herein is to reduce surficial microbes and germs of any kind on or on the transport containers of an inspection arrangement during operation by automatically disinfecting the transport containers on a regular, optional, or on-demand basis in parallel with the ongoing safety checks.

A first aspect provides a disinfection device for automatically disinfecting a transport container for transport through an inspection apparatus and for non-destructive inspection in the inspection apparatus of one or more inspection objects. In other words, the transport container serves to hold the one or more inspection objects and then serves as a container for transport through the inspection apparatus. The disinfection device has: an input point, at which emptied transport containers arrive and which is connected to a pick-up point of an inspection arrangement, at which inspected inspection objects can be picked up from the transport containers; an output point, which is connected to a lay-up point of the inspection arrangement, at which the transport containers can be placed and filled with one or more inspection objects; and at least one return conveyor for conveying the emptied transport containers over a return path extending from the input point to the output point. The solution proposed herein includes at least one automatic disinfection device arranged at the return path for disinfecting the emptied transport containers.

In some embodiments, the disinfection device of the first aspect can be integrated into an existing inspection arrangement for baggage inspection—such as for the inspection of hand luggage. Accordingly, an existing inspection arrangement can be improved by adding the disinfection device of the first aspect, since the transport containers can then be disinfected while in use. Removal or replacement of transport containers for cleaning is then no longer necessary. This means that the operation of the inspection arrangement is no longer impaired by handling for cleaning the transport containers. Also, fewer transport containers need to be kept in stock, since they are then essentially in continuous use.

A second aspect relates to an inspection arrangement for inspecting objects, such as carry-on luggage and other objects carried by persons, including: a lay-up point on which a transport container can be placed and filled with one or more inspection objects; a pick-up point at which the one or more inspection objects can be picked up from the transport container; an inspection apparatus, such as an X-ray inspection apparatus, for non-destructively inspecting the one or more inspection objects, the inspection apparatus being disposed between the lay-up point and the pick-up point; a conveyor apparatus extending through the inspection apparatus for conveying the transport containers through the inspection apparatus along an outward path extending from the lay-up point to the pick-up point; and a disinfection device for automatically disinfecting the transport containers according to an embodiment of the first aspect.

The following embodiments apply accordingly to the two preceding aspects.

The disinfection device may include at least one UV radiation unit for irradiating the emptied transport containers. The at least one irradiation unit may include one or more UV light units and optionally one or more reflector units arranged for irradiating the surfaces of the transport containers. In some embodiments, the one or more reflector units may irradiate the entire inner and outer surfaces of the transport containers. Such a configuration allows irradiation of the transport containers from different directions and guarantees complete disinfection of the entire surface.

For example, a UV radiation unit that generates UV-C beams can be used. In some embodiments, the mechanism of action of the UV-C disinfection is based on a purely physical rather than chemical basis, which avoids wetting the surface of the transport containers with a disinfection solution if this is not desired.

Alternatively or additionally, the disinfection device may include at least one spray unit with at least one spray nozzle configured for spraying the surfaces of the transport containers with a disinfection solution. In some embodiment the at least one spray nozzle may spray the entire inner and outer surfaces of the transport containers.

For example, the disinfecting solution may be a solution containing at least one of a bactericide, a fungicide, a sporicide, and a virucide, or any combination of these ingredients. Alternatively, the disinfecting solution may be hydrogen peroxide (H2O2); for example, a solution of water (H2O) containing 5-10%, and as another example, a solution of water (H2O) containing 7-8% H2O2. The disinfection solution may be held in one or more tanks, which is connected to the at least one spray nozzle by a connecting hose. The spray unit may further include a corresponding pump to deliver the disinfectant solution through the spray nozzle at the necessary pressure to enable uniform and complete spraying of the transport containers.

Alternatively or additionally, the disinfection device may include a heater for heating the disinfection solution. Thus, a corresponding high-temperature vapor consisting of the disinfecting solution is generated to improve the disinfecting effect. In this regard, the heater may be in communication with the tank of the disinfecting solution or directly with the injection nozzles. For example, H2O2 superheated steam can be used as the disinfectant.

Alternatively or additionally, disinfection can be performed using cold steam generated ultrasonically from the disinfectant solution. Again, a solution of H2O with H2O2 may be used as the disinfecting solution.

That is, the spray unit can be configured to generate a cold or hot spray mist or a cold or hot steam. Of course, the afore-mentioned spray variants can also be combined in the disinfection device. For example, hot steam disinfection can take place in a first area and cold steam disinfection in another area.

The one or more spray units can serve as the sole disinfection measure or can be combined with the UV radiation unit. This improves the disinfection effect.

The disinfection device may further include a mechanical cleaning unit, for example including a brush system with brushes arranged to mechanically act on the surface of the transport containers sprayed with disinfection solution. In this regard, the brush system can be designed such that one or more movable brush elements (e.g., rotating brushes) are in contact with the surface of the transport containers. In some embodiments, the brush system can be combined with the spray unit in order, for example, to additionally remove dirt from the transport containers and from their surfaces and, at the same time, to better distribute the disinfectant solution on the surfaces.

In addition to the at least one spray unit, the disinfection device may further include at least one heat radiation unit for irradiating and evaporating the disinfection solution present on the sprayed surface of the transport containers.

Alternatively or in addition to the heat radiation unit, the disinfection device may further include at least one drying unit for drying disinfection solution remaining on the surfaces of the transport containers. The at least one drying unit may include at least one heating device and/or a blower, such as a hot air blower. The drying unit may be located downstream of or adjacent to the spray unit.

In some embodiments, the return device may extend through or pass through the disinfection device.

The return device may be active or passive or may be configured as a combination of active and passive return conveying. "Active conveying" means that the return device actively conveys the transport containers, for example by means of a conveyor belt or driven transport segments driven for this purpose. "Passive conveying" means that the return device is designed in such a way that the transport containers move back automatically by means of gravity; for this purpose, the return device can be designed, for example, as an inclined plane with integrated stationary rollers, so that the transport containers, driven by gravity, move in the direction of the slope of the inclined plane.

In addition to all the above disinfection measures, the disinfection device may further include a tilting device or rotating device configured to change the position or arrangement of the transport containers during or in the course of a disinfection process. The tilting means may be configured, for example, as one or more projections arranged side by side, which may be referred to as tilting elements of the tilting means. While a transport container is on its way back, it abuts against a tilting element. Hereby, the initial position of the transport container is changed by the caused tilting function. Several tilting elements can be arranged one after the other in such a way that the transport container finally resumes the initial position and moves towards the output point or lay-up point. Thus a 360-degree disinfection of the transport container takes place. In order not to interfere with the movement of the return device, the tilting device may not be mounted directly on the return conveyor. For this purpose, the tilting elements can be fixed to the arrangement by a lateral holder, for example, without impeding the flow of movement of the return device.

The disinfection device may further include a control unit configured to control the disinfection device in accordance with a predetermined sequence or optionally activated or in dependence on a degree of contamination of the surfaces of individual transport containers; wherein "individual transport containers" means that the disinfection device selectively disinfects specific transport containers in accordance with a predetermined criterion.

To be able to be individually identified and thus selectively disinfected, the individual transport containers can be equipped with an identification feature that can be detected without contact and thus at a distance, for example an optically recognizable coding (a bar code or QR code marking) or an identification unit that can be read by radio (e.g., an RFID transponder). This allows, for example, the frequency of use of each transport container to be individually recorded and likewise individual disinfection/cleaning to be triggered, for example after a specified number of uses.

"According to a predefined sequence" means that the transport containers are disinfected, for example, according to a predefined temporal cycle, for example, after a predefined time interval, e.g., hourly.

"Optionally activated" means that the disinfection of the transport containers can optionally or exclusively be manually triggered by the operators of the inspection arrangement.

"Depending on a degree of contamination of the surfaces of individual transport containers" means that the disinfection and thus also cleaning of the transport containers can take place depending on the visually detectable contamination of the surfaces of the transport containers.

It is understood that the above principles can be used individually or in any combination and, if necessary, modified and, of course, with further strategies.

In the inspection arrangement proposed herein, the return device extends through the disinfection device. Thus, the transport containers can be disinfected as they move toward the output point or lay-up point along the return path.

In the inspection arrangement, the return path may extend at least partially below the conveyor passing through the inspection apparatus. Further, the inspection arrangement may include a lift device configured to lift the transport containers from the return path to a transfer path for the transport containers extending parallel to the lay-up point.

The disinfection device of the inspection arrangement may be located on the return path below the conveyor and/or in the lift device. For example, the lift device may include a vertically movable lifting floor in the manner of a Paternoster lift for lifting the containers back to the height of the transfer section.

In an alternative embodiment, the return path may extend adjacent to and at the level of the conveyor passing through the inspection apparatus. As discussed above, a portion of the return conveyor section may also be designed to allow the transport containers to return independently by gravity. The return path can also run laterally past the inspection apparatus back to the lay-up point of the inspection arrangement.

In some embodiments, the disinfection device of the first aspect or the inspection arrangement of the second aspect, the transport containers may be transport bins. Further, the transport bins may be made of a plastic material. As noted above, transport containers may each include a contactless detectable identification element, such as an optically detectable encoding and/or a radio readable RFID transponder.

Finally, it should be noted that the disinfection measures described above can all be suitably combined.

Initially, it is convenient to arrange the disinfection device below the conveying device of the outward section. Alternatively or additionally, the disinfection device can be arranged in the lift device. In this case, parts of the disinfection device can be arranged below the conveyor of the outward path and other parts can be arranged in the lift device. For example, the UV radiation unit and/or the spraying unit can be arranged on the return path below the inspection apparatus and the drying unit can be arranged directly in the lift device. If the complete disinfection device is positioned in the lift device, this results in a particularly compact modular arrangement that can be integrated particularly well into existing inspection arrangements (checkpoints).

Finally, a third aspect relates to a method for improving an existing inspection arrangement lacking a disinfection apparatus for the transport containers, including the step of integrating a disinfection apparatus in a return path for returning transport containers from the area behind the inspection apparatus to the area in front of the inspection apparatus.

BRIEF DESCRIPTION OF THE DRAWING FIGURES

Further advantages, features and details of the present disclosure will be apparent from the following description, in which certain embodiments are described in detail with reference to the drawings. In this connection, the features mentioned in the claims and in the description may each be essential individually or in any combination. Functionally similar or identical parts or components are partially provided with the same reference signs. The terms "left", "right", "top", "bottom" used in the description of the embodiments refer to the drawings in an orientation with normally readable figure designations or reference signs. Here schematically show:

FIG. 2a a schematic top view of a possible embodiment of an inspection arrangement of FIG. 1b;

FIG. 2b a schematic side view of the inspection arrangement of FIG. 2a;

DETAILED DESCRIPTION OF THE EMBODIMENTS

The following description sets forth numerous specific details of the solution disclosed herein. However, it is understood that further embodiments are also possible without these specific details. Circuits, structures, and methods known to those skilled in the art are not discussed in detail herein so as not to unnecessarily complicate the understanding of the present description. Terms "coupled" and "connected/connected" and terms derived therefrom are not used interchangeably herein. Rather, in specific embodiments, "coupled/connected" may indicate that two or more elements are in direct physical or electrical contact with each other. "Coupled" may imply that two or more elements interact or influence each other and may be in direct but also indirect physical or electrical contact with each other. Unless otherwise indicated, the use of the ordinal adjectives "first," "second," "third," etc. to designate a common object merely indicates that reference is made to various examples of like objects and is not intended to imply that the objects so designated must occur in some temporal, spatial, ranking, or other order.

Figure 1:
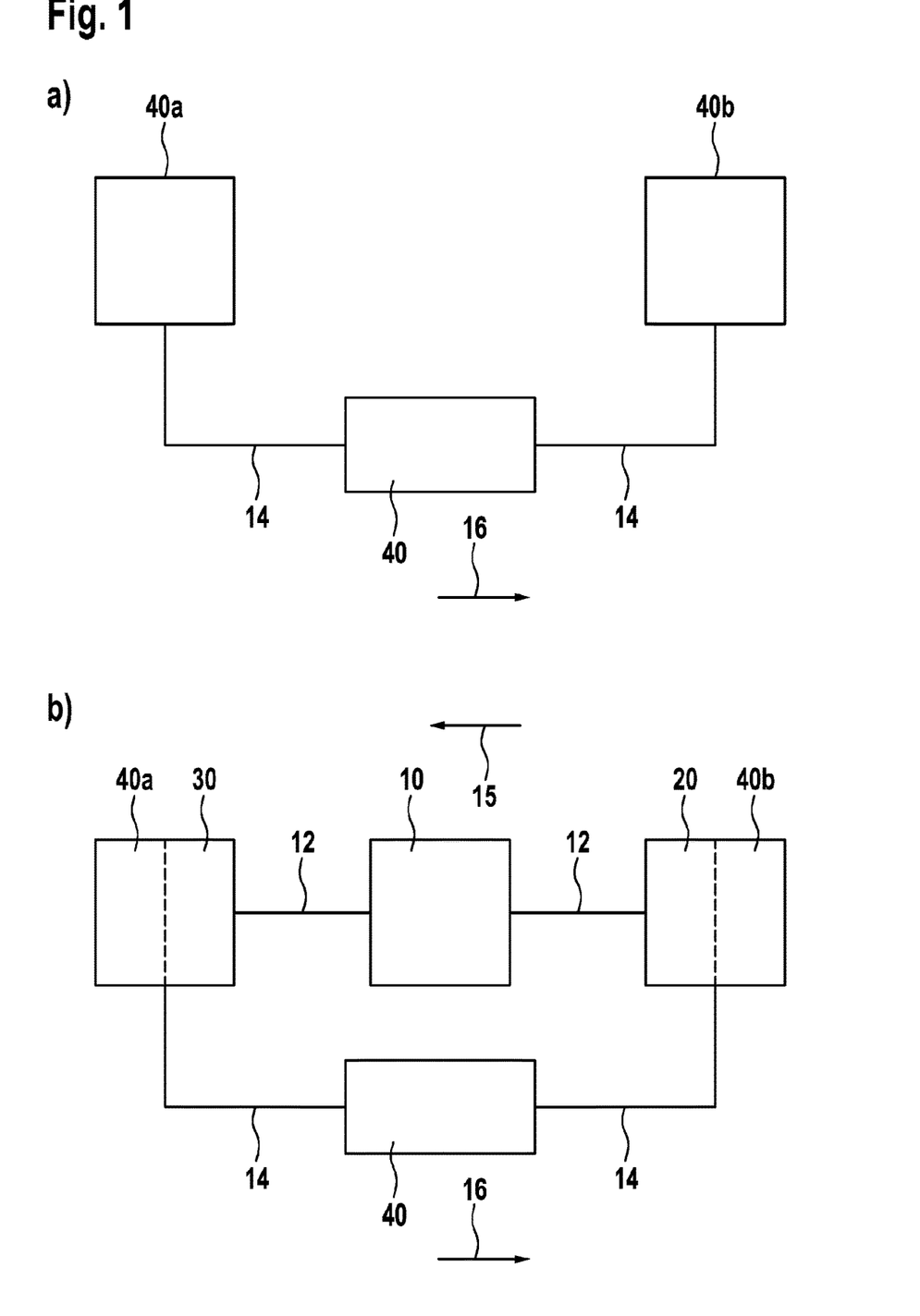
FIG. 1a a disinfection device of the first aspect shown in a block diagram.
FIG. 1b an inspection arrangement of the second aspect shown in a block diagram.

FIG. 1a schematically illustrates a block diagram of a disinfection device according to the first aspect. The disinfection device for automatic disinfection of transport containers 2 (not shown in FIG. 1a and from here on referred to as transport bins 2) has an input point 40a. At the input point 40a, the transport bins 2 arrive emptied, i.e., any inspection objects previously deposited therein have been picked up beforehand (e.g., at a pick-up point of an inspection arrangement, such as a checkpoint). The emptied transport bins 2 are conveyed along a return path 16 to an output point 40b via a return device 14. A disinfection device 40 is provided along the return path 16, which is configured for disinfecting the transport bins 2.

FIG. 1b schematically shows an inspection arrangement for inspecting inspection objects, such as carry-on luggage and/or other small items carried by a passenger at a checkpoint at an airport. The disinfection device of FIG. 1a can be integrated into the inspection arrangement in such a way that the input point 40a of the disinfection device is connected to the pick-up point 30 of the inspection arrangement and the output point 40b of the disinfection device is connected to the lay-up point 20 of the inspection arrangement.

In FIG. 1b, the input point 40a and the pick-up point 30 or the output point 40b and the lay-up point 20 are in direct contact with each other. Of course, these could also be connected to each other by one or more intermediate elements (e.g., conveyor belt, roller conveyor or other devices). Here, a transport bin 2 present at the lay-up point 20 and filled with articles is conveyed through an inspection apparatus 10 by means of an outward conveying device 12. In the inspection apparatus 10, a safety check of the objects as inspection objects is carried out in an imaging and non-destructive manner known per se, for example by means of X-ray inspection. After the inspection objects located in the transport bin 2 have been checked, they reach the pick-up point 30 via the outward path 15, at which the objects that have now been checked and found to be safe may be picked up again from the transport bin 2 by the owner. The emptied transport bin 2 then reaches the input point 40a of the disinfection device. As already described in connection with FIG. 1a, the transport bin 2 is disinfected by means of the disinfection device 40 on its way back to the output point 40b. The disinfected transport bin 2 then returns to the lay-up point 20 and is available, disinfected, for a new work cycle.

Figure 2:
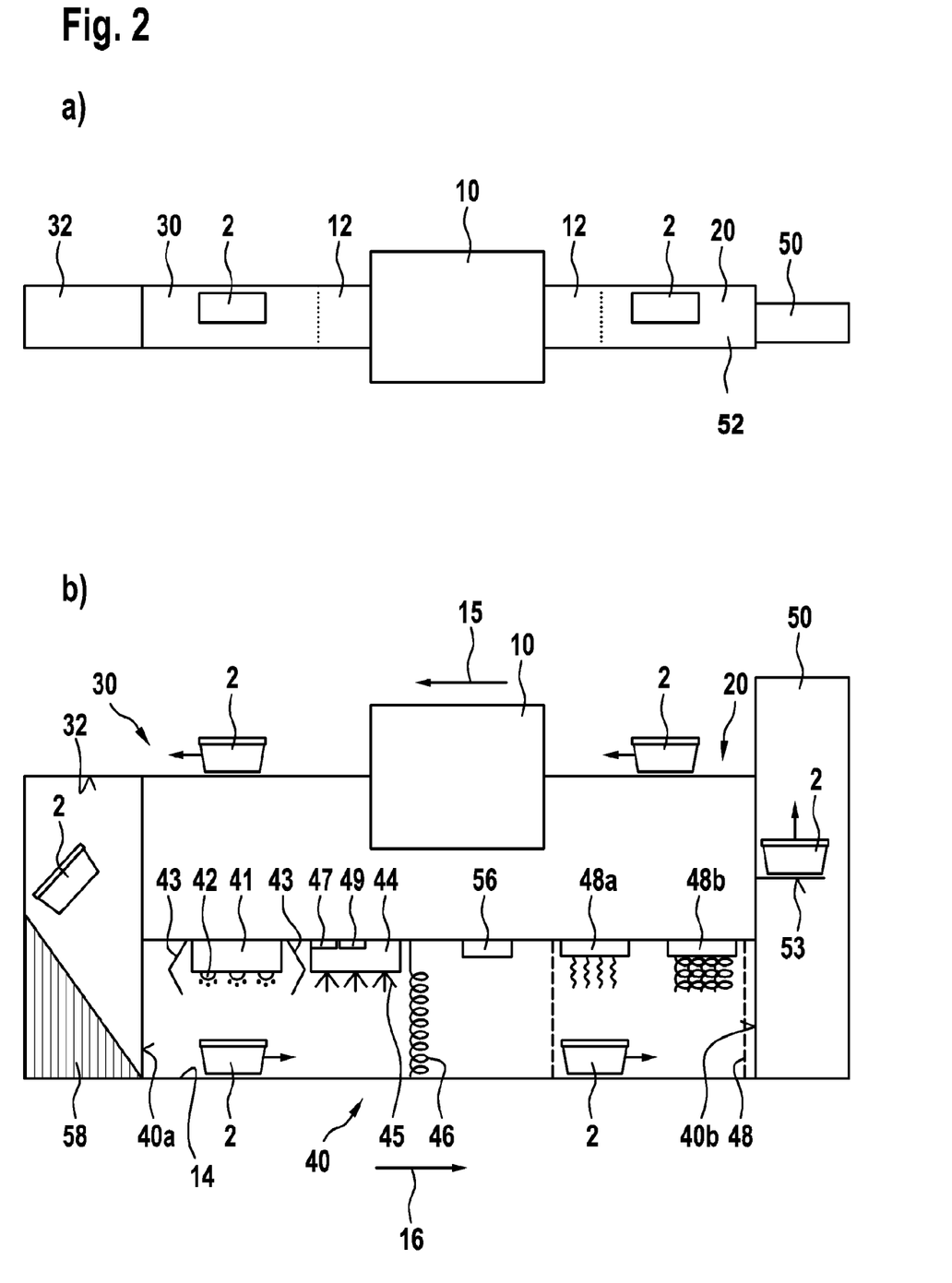
Figure 3:
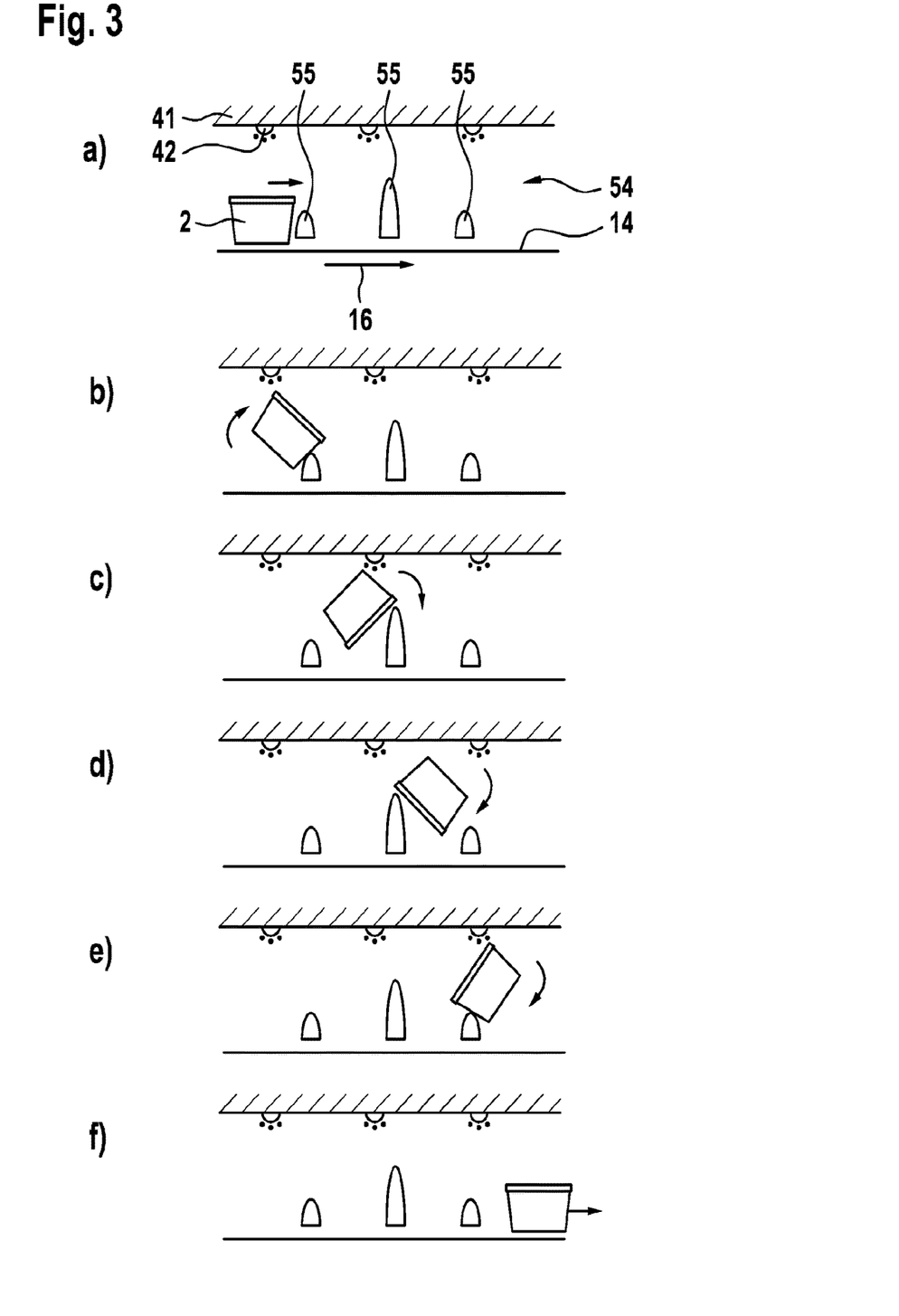
FIGS. 3a-f a sequential illustration of a tilt arrangement for the disinfection device of the first and second aspects.

FIGS. 2a and 2b show an inspection arrangement (checkpoint), where FIG. 2a is a top view and FIG. 2b is a side view of the inspection arrangement. For example, such an inspection arrangement can be used at an airport for security checks of hand luggage and other items carried by passengers.

In FIG. 2a, the transport bins 2 arrive at the lay-up point 20 via a bin lift 50 provided as a lifting device by means of a bin transfer section 52. From here, passengers can deposit their items (e.g., laptop, shoes, small bags, purse, etc.) in the transport bins 2 and be conveyed through an inspection apparatus 10 by means of the outward conveyor 12. After passing through a security check by means of non-destructive and imaging inspection of the items as inspection objects, the transport bins 2 reach the pick-up point 30, where the passengers are allowed to pick up their inspected and found safe items from the transport bin 2 again. The previously used and then emptied transport bins 2 are returned to the lay-up point 20 by a return path 16.

As shown in FIG. 2b, the return path 16 is located below the inspection apparatus 10. To get from the pick-up point 30 to the input point 40a, the transport bins 2 pass through an intermediate element here as a sliding element 58, which is provided with a slide point 32. Now the transport bins 2 are on the return device 14 and are passed through a disinfection device 40.

In the example shown, the disinfection device 40 includes various disinfection processes arranged in series and housed within a closed structure, such as a housing. The structure may be tunnel-shaped, for example, and have an input and an output.

Each individual disinfection process is associated with a particular unit within the disinfection device 40. According to a particular embodiment, elements forming these units may be arranged or attached above the return device 14 or directly to the ceiling of the structure, for example the housing forming the disinfection device 40.

In the example shown, the transport bins 2 are first irradiated by means of UV lamps 42 of a radiation unit 41. Reflectors 43 are also provided in the radiation unit 41 to enable the UV beams to be reflected around the transport bins 2 so that, as far as possible, the entire surface of the transport bins 2 is reached.

Next, the transport bins 2 pass through a spray unit 44 in which the transport bins 2 are sprayed with a disinfecting solution using spray nozzles 45. The disinfecting solution is in a container 49, which can be heated by means of an associated heater 47, which interacts with the spray nozzle 45, for example. Thus, the disinfectant solution can be used in the form of steam (as superheated steam) or at least hot, which on the one hand increases the disinfection effect, but also allows the disinfectant solution to dry more quickly. Alternatively or additionally, the spray unit 44 can also be configured to generate cold steam, for example by means of ultrasonic vaporization.

In the example shown, an optional brush system 46 is additionally arranged in the spray unit 44, on the one hand to remove any surface impurities, such as dirt residues and/or particles, from the surface of the transport bins 2, but also to better distribute the disinfection solution on the surface of the transport bins 2.

Next, the transport bins 2 pass through a drying unit 48, which provides a heating device 48a followed by a blower 48b. The combination of heat and air flow ensure that the transport bins 2 emerge as dry as possible at the output of the disinfection device 40.

Immediately after the output of the disinfection device 40, the bin lift 50 with lifting floors 53 is installed, by means of which the transport bins 2 return to the lay-up point 20.

The input and output of the disinfection device 40 correspond to the input point 40a and output point 40b of the inspection arrangement, respectively. The disinfection device 40 is also equipped with a control unit 56 that is connected to and controls all units (radiation unit 41, spray unit 44, drying unit 48).

FIGS. 3a to 3f show the movement of a transport bin 2 within a radiation unit 41, in which a tilting device 54 is integrated. In this case, the tilting device 54 includes a plurality of tilting elements 55 arranged in succession, which are attached to the structure or housing of the disinfection device 40 in such a way that these tilting elements 55 do not obstruct the direction of travel of the return device 14. The individual tilting elements 55 may differ from each other by different shapes and sizes, to allow the tilting or the change of the support of the transport bin 2.

For example, FIGS. 3a to 3f show three different tilting elements 55, of which the central element is of a higher configuration relative to the two outer elements. This allows complete rotation of the transport bin 2, as made visible by the arrows in FIGS. 3b to 3e.

Figure 4:
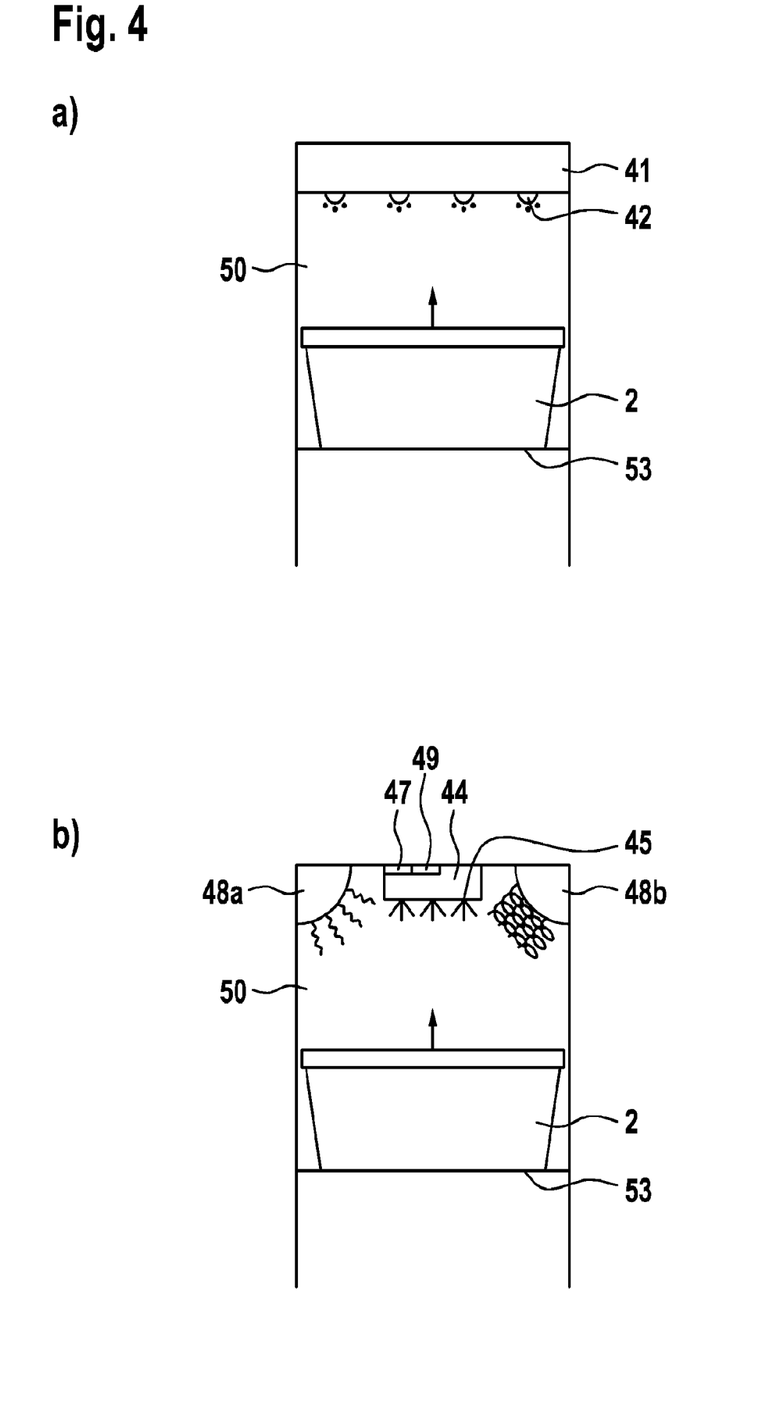
FIG. 4a a schematic representation of a radiation unit integrated in a lift device.
FIG. 4b a schematic representation of a spraying unit integrated in a lift device.

FIG. 4a shows an example of a bin lift 50 in which a radiation unit 41 has been integrated. Here, the UV lamps 42 of the radiation unit 41 are arranged on the ceiling of the bin lift 50 to enable irradiation of the transport bin 2 during elevation on the lifting floor 53.

FIG. 4b shows an alternative bin lift 50 in which a spray unit 44 is integrated. Here, the spray nozzles 45 are arranged on the ceiling of the bin lift 50 to enable distribution of the disinfection solution to the transport bin 2 during raising on the lifting floor 53. In addition, a heating unit 48a and a blower 48b are provided on the ceiling of the bin lift 50 for drying the transport bins 2.

Via the control unit 56, the spraying unit 44 and the heating unit 48a as well as the blower 48b are controlled in time sequence so that drying takes place immediately after the spraying of the transport bin 2 is completed.

If the disinfection device 40 is completely integrated in the bin lift 50 (cf. FIGS. 4a and 4b), the input and output of the bin lift 50 correspond to the input point 40a and the output point 40b of the arrangement.

What is claimed is:

1. Disinfection device for the automatic disinfection of a transport container intended for the transport of one or more inspection objects through an inspection apparatus and their non-destructive inspection in the inspection apparatus, the disinfection device comprising:
    an input point at which emptied transport containers arrive and which is connected to a pick-up point of an inspection arrangement at which inspected inspection objects can be picked up from the transport containers,
    an output point which is connected to a lay-up point of the inspection arrangement at which the transport containers can be placed and filled with one or more inspection objects,
    at least one return device for conveying the emptied transport containers along a return path extending from the input point to the output point, and
    at least one automatic disinfection device arranged at the return path for disinfecting the emptied transport containers.

2. The disinfection device according to claim 1, wherein the disinfection device comprises at least one UV radiation unit for irradiating the emptied transport containers.

3. The disinfection device according to claim 2, wherein the at least one radiation unit comprises one or more UV light units and one or more reflector units arranged for irradiating the surfaces of the transport containers.

4. The disinfection device according to claim 3, wherein the one or more UV light units and one or more reflector units are arranged for irradiating the entire inner and outer surfaces of the transport containers.

5. The disinfection device according to claim 1, wherein the disinfection device comprises at least one spray unit with at least one spray nozzle, which are configured for spraying the surfaces of the transport containers with a liquid or vaporous disinfection solution.

6. The disinfection according to claim 5, wherein the disinfection device further comprises a brush arrangement comprising static and/or rotating brushes arranged to mechanically act on the surface of the transport containers sprayed with disinfection solution.

7. The disinfection device according to claim 5, wherein the disinfection device further comprises at least one heat radiation unit for irradiating and evaporating the disinfection solution present on the sprayed or vaporized surface of the transport containers.

8. The disinfection device according to claim 5, wherein the disinfection device further comprises at least one drying unit for drying disinfection solution remaining on the surfaces of the transport containers, wherein the at least one drying unit comprises at least one heating device and/or a blower.

9. The disinfection device according to claim 8, wherein the at least one drying unit comprises at least one blower that is a hot air blower.

10. The disinfection device according to claim 5, wherein the at least one spray nozzle is configured for spraying the entire inner and outer surfaces of the transport containers.

11. The disinfection device according to claim 1, wherein the return device extends through the disinfection device.

12. The disinfection device according to claim 1, wherein the disinfection device further comprises a tilting device for changing the position of the transport containers during a disinfection process.

13. The disinfection device according to claim 1, wherein the disinfection device further comprises a control unit for controlling the activation of the disinfection device according to a predetermined sequence or selectively or in dependence of a degree of contamination of the surfaces of individual transport containers.

14. An inspection arrangement for inspecting inspection objects, such as carry-on luggage and other objects carried by persons, the inspection arrangement comprising:
    a lay-up point on which a transport container can be placed and filled with one or more inspection objects;
    a pick-up point at which the one or more inspection objects can be picked up from the transport container; and
    an inspection apparatus, for the non-destructive inspection of the one or more inspection objects, the inspection apparatus arranged between the lay-up point and the pick-up point,
    an outward path extending through the inspection apparatus for conveying the transport containers through the inspection apparatus along an outward path extending from the lay-up point to the pick-up point, and
    a disinfection device for automatic disinfection of the transport containers according to claim 1.

15. The inspection arrangement according to claim 14, wherein the return path extends at least partially below or next to the outward conveyor device leading through the inspection apparatus and further comprises a lifting device which lifts the transport containers from the return path to a transfer path for the transport containers extending parallel to the lay-up point.

16. The inspection arrangement according to claim 15, wherein the disinfection device is arranged at the return path below or next to the outward conveyor and/or in the lift device.

17. The inspection arrangement according to claim 14, wherein the return path runs wholly or partly as an inclined plane next to the outward conveyor device leading through the inspection device and is configured for conveying the transport containers by means of gravity.

18. The inspection arrangement according to claim 14, wherein
- the transport containers are transport bins, and/or
- the transport containers each have an identification element that can be detected without contact, such as an optically detectable coding and/or an RFID transponder that can be read by radio.

19. The inspection arrangement according to claim 14, wherein the inspection apparatus is an X-ray inspection apparatus.

20. The disinfection device according to claim 1, wherein
- the transport containers are transport bins, and/or
- the transport containers each have an identification element that can be detected without contact.

* * * * *